(12) United States Patent
Kuhn

(10) Patent No.: US 6,213,770 B1
(45) Date of Patent: Apr. 10, 2001

(54) HANDPIECE FOR MEDICAL OR DENTAL PURPOSES HAVING A SETTABLE STOP DEVICE

(75) Inventor: Bernhard Kuhn, Schemmerhofen (DE)

(73) Assignee: Kaltenbach & Voigt GmbH & Co., Biberach/Rib (DE)

( * ) Notice: Subject to any disclaimer, the term of this patent is extended or adjusted under 35 U.S.C. 154(b) by 0 days.

(21) Appl. No.: 09/352,435

(22) Filed: Jul. 13, 1999

(30) Foreign Application Priority Data

Jul. 14, 1998 (DE) .............................................. 198 31 568

(51) Int. Cl.$^7$ ...................................................... A61C 3/00
(52) U.S. Cl. ................................. 433/75; 433/72; 433/102
(58) Field of Search .................................. 433/114, 116, 433/102, 75, 72

(56) References Cited

U.S. PATENT DOCUMENTS

| 1,321,129 | * | 11/1919 | Schlueter | 433/76 |
| 2,621,408 | * | 12/1952 | Klein | 433/76 |
| 2,703,453 | * | 3/1955 | Landis | 433/75 X |
| 3,346,959 | * | 10/1967 | Fridge | 433/76 |

FOREIGN PATENT DOCUMENTS

| 40 17 038 A1 | 4/1991 | (DE) . |
| 40 26 011 A1 | 2/1992 | (DE) . |

\* cited by examiner

*Primary Examiner*—Nicholas D. Lucchesi
(74) *Attorney, Agent, or Firm*—Marshall, O'Toole, Gerstein, Murray & Borun

(57) ABSTRACT

The invention relates to a handpiece (1) in particular for medical or dental purposes, having a connection device (3) for a tool (4) which is arranged in the forward end region of the hand piece (1), and having a settable stop device (6) for limiting the penetration depth of the tool (4), which stop device has a stop part (7), which is adjustable in a guide (8) longitudinally of the penetration depth of the tool (4) and is secured in the respective adjusted position by means of a clamping force (11). For the purpose of more ready setting of the stop part the clamping force (11) is elastic and on the one hand is so great that it secures the stop part (7) against displacing forces effective in functional operation, and on the other hand is only so large that the stop part (7) can be manually displaced, and in that the stop part (7) is of a hard elastically bendable material and sits in the guide (8) bowed so far that its return bending force (11a) gives rise to the clamping force (11).

9 Claims, 2 Drawing Sheets

HANDPIECE FOR MEDICAL OR DENTAL PURPOSES HAVING A SETTABLE STOP DEVICE

Figure 2:
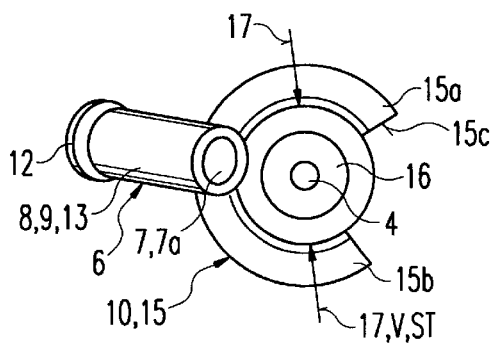

The invention relates to a handpiece in particular for medical or dental purposes, having a connection device for a tool disposed in the forward end region of the handpiece, and having a settable stop device for limiting the penetration depth of the tool. In one embodiment, the stop device has an element which is adjustable in a guide longitudinally of the penetration depth of the tool, and is secured in the adjusted position by means of a clamping force.

Such a handpiece has already been proposed. It can be used for various treatment or working measures on the human or animal body. In such cases in which a particular penetration depth of the tool of the handpiece is of significance, there has already been proposed a stop device on the handpiece having a stop part the axial spacing of which to the tool tip is so settable that different penetration depths for the tool can be set. For fixing the stop part of the stop device in the position set in each case there may serve a fixing device, effective either in a form-locking or force-locking manner, e.g. a screw drive or a clamping screw, with which the stop part is manually adjustable and is secured in the set position in a form-locking manner or with which the stop part can be fixedly clamped. In both cases, a special component must be moved.

With these known configurations there is thus needed a considerable manual effort in order to set the penetration depth on the stop device. Although a screw drive ensures an easy adjustment due to an integrated step-down gearing, in particular with large adjustment measures, such as occur in particular in the preparation of tooth root canals, can be set only with a relatively great expenditure of time, whereby for the setting the screw drive is to be continuously operated. In the other case, the release and fixing of the clamping screw is also expensive in terms of manipulation and time.

The object of the invention is to so configure a handpiece of the kind described above that a readily manipulable and rapid setting of the stop part along the penetration depth is possible.

This object is achieved by means of the a handpiece wherein the clamping force is elastic and on the one hand is so great that it secures the stop part against displacing forces effective in functional operation, and on the other hand is only so large that the stop part can be manually displaced, and in that the stop part is of a hard elastically bendable material and sits in the guide bowed so far that its return bending force gives rise to the clamping force.

With the handpiece in accordance with the invention there is no need for releasing and tightening of the setting device at the stop device; rather for a setting, the stop part can be directly manually grasped and adjusted, whereby merely a certain application of force is to be provided in order to adjust the stop part. The fixing of the stop part and the respective set position is effected automatically by means of the elastic clamping force, which is so great that the stop device is capable of taking up the impact forces appearing in functional operation of the handpiece without being displaced, and on the other hand is only so large that the stop part can be adjusted by means of the manual pushing or pulling force, whereby the elastic clamping force is overcome. The configuration in accordance with the invention distinguishes itself also by means of a simple and compact construction. The first is based upon the fact that no additional and movable clamping part is needed, so that the stop device can be provided in simple and compact construction, which with regard to the restricted space availability at possible treatment sites of the human or animal body and in particular in the case of a dental handpiece is of substantial significance.

Further, with the configuration in accordance with the invention, there is no need for actuation of a setting drive such as is the case with a screw drive; rather the stop part is directly displaced in its adjustment movement, and great drive travel and intermediate gearings, which also lead to a bulkier construction, are not needed.

In functional operation, the respective stop points are different from treatment site to treatment site, and thus there is needed a setting of the position of the stop part with regard to the respective stop position concerned. For this purpose it has also been previously proposed to arrange the stop part transversely adjustably and fixable in the respective adjusted position by means of a clamping screw.

Furthermore, the arrangement of a stop device, in particular at the forward end of the handpiece, is problematic in two regards considering the resulting constructional size. On the one hand, the provision of a stop device leads to an increase in size of the handpiece, and on the other hand the view of the treatment site is hindered, both if the direction of viewing is directed along the tool axis taking into account a small angle of inclination, and when it is transverse thereof. In the first case, any broadening of the handpiece head is in principle undesired. In the second case the stop part itself is the main disruption, which stop part extends up to the treatment site and by engagement restricts the working depth.

Thus, the present invention has the further object of so configuring a handpiece of the kind having a connection device for a tool, wherein the connection device is disposed in the forward end region of the hand piece, and having a stop device for limiting the penetration depth of the tool wherein the stop device has a stop part which is adjustable transversely of the penetration depth and is secured in the adjusted position against an unintended displacement by means of a clamping part, so, that a readily manipulable and rapid setting of the stop part, transverse to the penetration depth, is possible.

This object is achieved by means of a clamping part which stands under an elastic clamping tension, which on the one hand is so great that it secures the stop part against displacing forces effective in functional operation and on the other hand is only so large that the stop part is manually adjustable, and in that the clamping part of the stop device is a C-shaped clasp which is disposed on a holding pin, the cross-sectional shape of which is circular or cornered.

By means of this configuration, the same advantages are attained as have already been indicated with the configuration of the invention described earlier herein, with the difference that in this case transversely directed forces and movements are concerned.

In functional operation, one of a plurality of stop positions at the tissue can be sought out which are particularly well suited for a stop, or where a stop is possible at all. With regard to this posed problem, the handpiece in accordance with the invention is thus adaptable and the best stop position in a particular range of movement can be sought out.

Further, the stop device with the configuration according to claim 6 can be moved between a non-use disposition, in which the stop device is located, so to say, in a not needed parking position, and where it does not hinder the view of the treatment site, into a use position in which a good stop position is located or even where a stop is at all possible.

This configuration in accordance with the invention is also, with regard to a right-handed/left-handed usability of the handpiece of advantage and in particular when the stop device can be moved from the one side of the handpiece to the other side of the handpiece, and is thus settable for a right-handed and left-handed function. These basic settings are independent of the setting of the stop part in the direction of the penetration depth.

Further, the invention has the object of so configuring a handpiece of the kind having a connection device for a tool which is disposed in the forward end region of the handpiece, and having a stop device for limiting the penetration depth of the tool, which has a stop part which is adjustable preferably longitudinally and/or transversely of the penetration depth of the tool and is secured in the adjusted position by means of a clamping force so, that it is employable for work with and without penetration depth limiting.

This object is achieved by means of the stop device connectable with, and releasable from, the handpiece by means of a latching device for plug-in/clamping device.

With this configuration, the stop device is connected with the handpiece by means of a latching device or a plug-in/ clamping device, and is thus readily manipulably and rapidly mountable and releasable. By these means, the stop device can, when it is needed, be rapidly mounted on the handpiece and, when it is not needed, rapidly dismounted.

For these measures, a latching device or plug-in/ clamping device is eminently suitable, since they make possible a rapid and also readily manipulable mounting and dismounting, and also ensure a compact construction.

In particular in consideration of the above-described restricted space availability and freedom of view of the treatment site, both the position of the stop device with regard to the handpiece and also the fixing location of the stop device on the handpiece, are of significance. An advantageous fixing point is located directly before the end face of a handpiece or of a handpiece head (angled piece), in the region surrounding the vicinity of the tool. This region is preferably formed by means of an additional piece, in particular an annular additional piece, on the end face concerned, on which the stop device can be attached, preferably by means of the latching device or the plug-in clamping device. This above-described position does not disrupt the view of the treatment site, because the angle of view is directed laterally alongside the handpiece and handpiece head and thus also runs alongside this treatment site. If the stop part is then arranged also in the vicinity of the tool, not only the attachment position but also the stop part can be located within the projection range of the handpiece given longitudinally of the tool, so that not only the attachment point but also the stop part does not hinder, or hardly hinders, the view. For this reason, this attachment point and the associated features of configuration are of inventive significance on their own.

Further, the present invention relates to the stop device itself in accordance with the invention.

The the invention also provides features which, furthermore, lead to small, readily manipulably operable and economically manufacturable configurations, and distinguish themselves through a good functionality and long operating life.

The stop device is a component which can be selectively mounted on the handpiece. The invention is thus concerned also with the stop device as a separate part.

Figure 1:
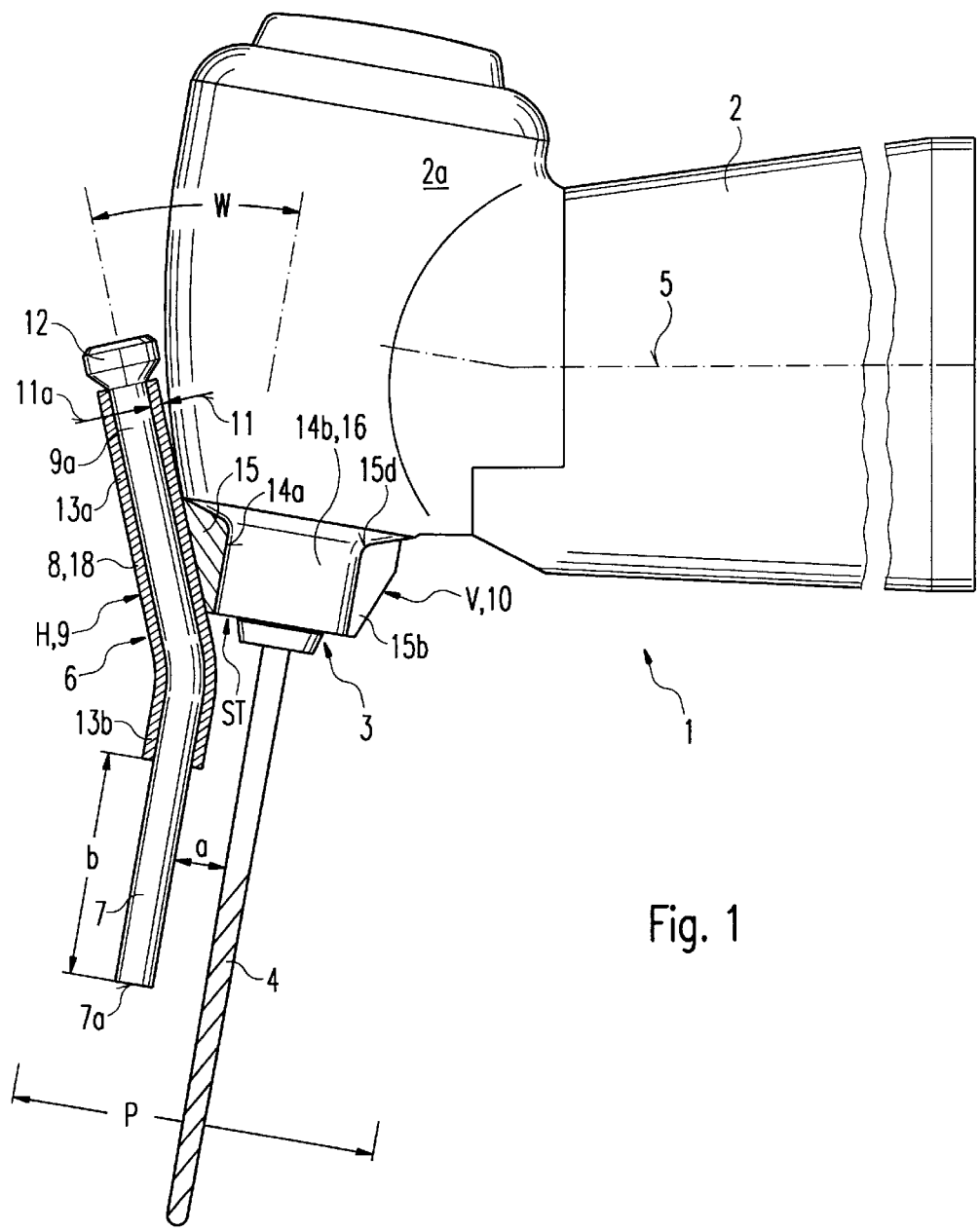
Figure 4:
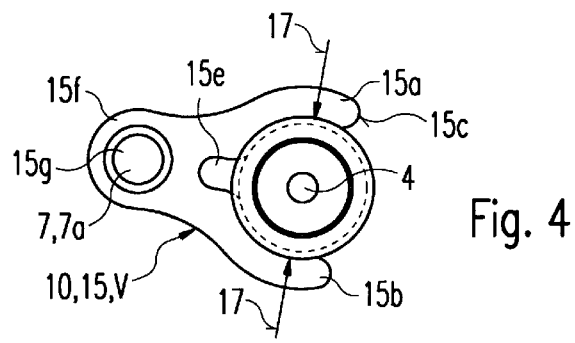
Figure 3:
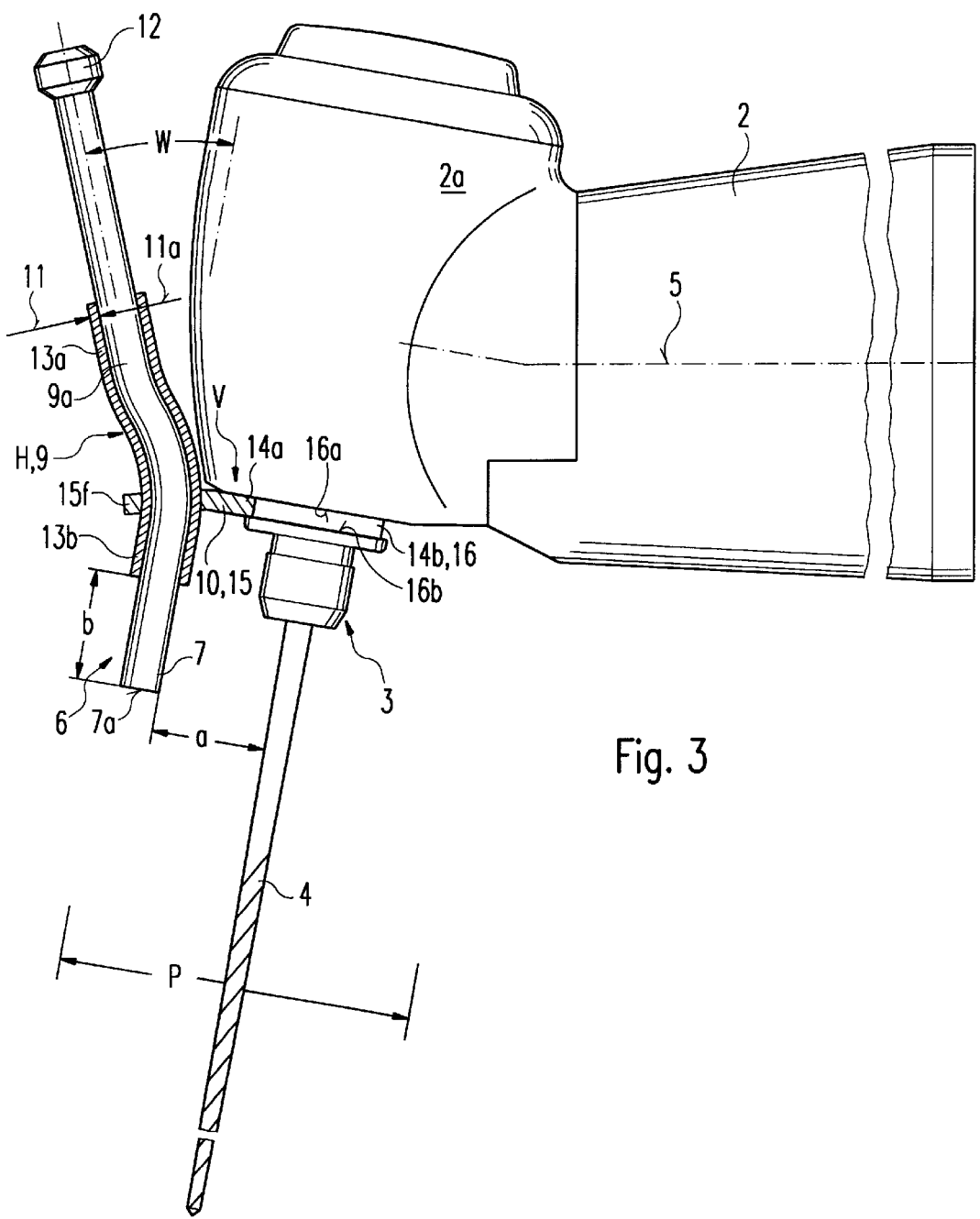

Below, the invention and further advantages which can be achieved thereby, will be described with reference to advantageous exemplary embodiments. There is shown:

FIG. 1 the forward end region of a dental handpiece in accordance with the invention, having a stop device;

FIG. 2 the stop device in a view from below;

FIG. 3 the forward end region of the dental handpiece in accordance with the invention, with a stop device in a modified configuration;

FIG. 4 the stop device in accordance with FIG. 3, in a view from below.

The handpiece designated 1 has a grip sleeve 2 which may extend straight or angled, as is usual for dental handpieces, and at its forward end has integrally a connection device 3, e.g. a mounting or holding device, for a tool 4, which maybe e.g. a chip removing tool 4. In the present configuration, the elongate tool 4 extends transversely of the longitudinal middle axis 5 of the handpiece. Such a handpiece 1 is designated in the terminology of this art as an angled head. Within the scope of the invention, however, the tool may also extend forwardly, longitudinally of the middle axis 5 of the handpiece.

In the handpiece 1 there is arranged a drive device for the tool 4. This may be a drive chain (not shown), which upon coupling of the rearward end of the grip sleeve 2 to a so-called connection part is connected directly or indirectly with a motor arranged in the connection part. The handpiece 1 may also be a so-called turbine having a turbine drive in the forward end region of the handpiece 1 which is fed with compressed air from a supply line which, upon the above-described coupling of the grip sleeve to the connection part, is coupled with an associated supply line section. With the present exemplary embodiment, the tool 4 is thin and relatively long flexible root canal tool, which serves for the preparation of the root canal of a tooth. At the handpiece 1 there is releasably attached a stop device 6 having a pin-shaped stop part 7, the forward end region of which is arranged in the vicinity of the tool set back from the forward end thereof, and forms a stop 7a.

The main parts of the stop device 7 are the stop part 7 in the form of a pin having a preferably round cross-section, a guide 8 in which the stop part 7 is arranged and is longitudinally displaceable, and elastically effective clamping device 9, which exercises a transversely directed clamping force on the stop part 7 which is at least so great that the impact forces acting against the stop part 7 in functional operation can be taken up without the stop part 7 being displaced in the guide 8, and on the other hand is only so great that the stop part can be manually grasped and displaced in the guide 8 by the exercise of a certain pushing or pulling force. Thereby, the transversely directed elastic clamping force, indicated by the arrow 11, is overcome. In order to facilitate the manual grasping of the stop part 7 this has in an end region a waist part or a thickening, e.g. a thickened head 12, preferably at the end of the stop part 7 away from the tool tip. It is of a relatively hard material which due to its elongate or pin-like form is transversely elastically bendable, and is preferably of plastics.

The guide 8 is formed by means of an angled tube 13 to the inner cross-sectional size of which the stop part 7 is adapted with a slight play for movement so that it is readily manually displaceable in a straight extending section of the tube 13. Due to the angling of the tube, e.g. by an angle W of about 30°, the straight stop part 7 is compelled to take up the angled shape, i.e. upon insertion into the tube 13, the stop part 7 is bent into the angle shape. By these means, in the stop part 7, due to its elasticity, a return bending force 11a arises, which permanently presses against the tube wall and thereby due to the surface friction present generates the elastic clamping force 11, whereby the bent limb of the stop part functions itself as transversely moveable clamping part 9a. The magnitude of the clamping force 11 is dependent upon the angle W and can be predetermined by means of a greater or smaller angle W. The angling of the tube 13 is in the peak region preferably not sharp, but rather rounded or curved.

The stop device 6 is connected with the handpiece 1 by means of a releasable quick-fastening connection, which is preferably formed by means of a plug-in/clamping device ST or a latching device V. For this purpose, there are arranged on the stop device 6 a device part 14a and on the handpiece 1, a device part 14b, which are elastically latchable with one another, whereby upon latching and upon un-latching in each case one of the two latch parts 14a, 14b can be elastically bent out and thereby overcome with a certain effort of force.

With the present configuration, the device part 14a or the clamping part 10 is formed by means of a C-shaped clasp 15 with two clasp arms 15a, 15b, arranged claw like, of elastically bendable material, which can be pushed on to an e.g. cylindrical holding pin 16 on the handpiece 1, whereby upon pushing on the clasp arms 15a, 15b are first spread and then engaged behind the holding pin 16 and press against the holding pin 16. By these means there is generated a radially inwardly directed clamping force 17, which due to the friction restricts a rotation of the stop device 6 around the holding pin 16. Only with a somewhat increased manual rotation force can the clasp 15 be adjusted in the circumferential direction, steplessly, on the holding pin 16, whereby it secures the respective set rotational position in each adjusted position due to its clamping force 17. Upon transversely directed displacement on to the holding pin 16, the end faces of the holding arms 15a, 15b form oblique guide-in surfaces 15c. This clasp 15 has an axial length which approximately corresponds to the diameter of the holding pin 16 and is thus in substance sleeve-shaped, whereby a stable holding is attained.

The axial position of the stop device 6 is determined by means of its abutment on a shoulder surface 16a of the holding pin 16, which is here arranged on the end of the holding pin 16 away from the tool tip and may be cone-like.

The function of the plug-in/clamping device ST, in the sense of a plug-in mounting, is in particular clear if the fork 15 is plugged axially onto the holding pin 16, whereby a corresponding hollow cone-shaped end surface of the clasp 1 or an obliqueness or rounding 15d of the inner hole edge forms a guide-in surface which facilitates the axial pushing on.

The radially inwardly directed clamping force 17 of the latching or clamping device V, ST is so dimensioned that due to the resulting clamping an undesired rotation of the stop device 6 upon use of the handpiece is prevented. In contrast, the stop device 6 can be rotated by means of manual application of force, whereby the clamping 17 is overcome and in the respectively steplessly settable rotational position is again automatically effective. With the present configuration, the clasp arms 15a, 15b are circular arc-shaped inwardly rounded, whereby in the relaxed condition the radius is somewhat smaller than the diameter of the holding pin 16.

The tube 13 is on the one hand attached to the clasp 15 in its middle region (tube limb 13a) or in the region of its angle peak (FIG. 3) and on the other hand attached to the clasp 15 in the region of the peak of the clasp 15. The spacing a of the tube limb 13b towards the tool tip and extending parallel to the tool 4 is a few millimetres and can be predetermined taking into account particular application cases. With the present handpiece 1 for the preparation of root canals, the spacing a is about 2 to 4 mm, so that the stop part 7 in functional operation abuts with its forward end stop 7a against the occlusal edge region of the tooth concerned and restricts the penetration depth.

In the disposition illustrated in FIG. 1, the stop part 7 is located in its forwardmost position. The spacing b present in this position from the forward end of the guide tube 13 can serve as the setting range. The tube limb 13a extends alongside the handpiece 2, here alongside its angled head 1a. For the purpose of linear abutment of the tube 16 on the clasp 15 the envelope surface of the clasp 15 is correspondingly cone-shaped at least in its forward region. The attachment of the tube 16 can be effected e.g. by means of gluing or soldering or welding.

The exemplary embodiment according to FIGS. 3 and 4—in which the same or similar parts are provided with the same reference signs—differs from the above-described exemplary embodiment in the following details. The clasp 15 is, in the manner of a plate, more thin and may be of sheet material. Its thickness maybe e.g. about 1 to 2 mm. By this means it is possible to manufacture the clasp 15 as a stamped part, which is very economical. In view of the slight thickness, the width of the clasp arms 15a, 15b should be somewhat larger, whereby the elasticity is reduced. In particular with such a clasp 15 it is advantageous to arrange in the peak region of the clasp 15 a recess 15e which increases the elasticity of the clasp arms. As is further shown in FIG. 3, the clasp has in a base web 15f a hole 15g through which the tube 16 extends. Further, the clasp 15 maybe angled in its base region, so that the tube 16 penetrates the here angled base web 15f approximately at right angles.

A further difference of the configuration according to FIG. 3 consists in that the guide tube 13 has two mutually opposite anglings, preferably being curved in an S-shape. By these means, the clamping tension 11 or the return bending tension 11a can be increased. In this representation, the stop part 7 is located in a middle position of the available adjustment range.

A further difference consists in that the holding pin 16 does not only have a shoulder surface 16a on its side away from the tool tip, but also has on its side towards the tool tip a shoulder surface 16b with slight insertion play, whereby the clasp 15 sits in a groove, preferably an annular groove, and is stabilized and secured in both axial directions.

The diameter of the holding pin 16 is smaller than the cross-sectional dimension of the handpiece 2, here that of the angled head 2a. Consequently, the holding pin 16, the clasp 15 and the axis-parallel tube limb 13b are arranged in the axial projection surface P of the handpiece 2, where they do not or hardly adversely effect the angle of view, at an acute angle to the tool axis, on to the treatment site.

When the holding pin 16 has a plurality of corners, e.g. two corners, four corners, six corners, eight corners or is formed in the manner of a multi-tooth shaft, there can be set in steps, in the circumferential direction, defined latching dispositions in particular rotational positions.

The individual parts of those forming a holding device H for the stop part 7, here the guide tube 13 and the clasp 15, may likewise be of hard plastics or steel, in particular spring steel.

The configurations in accordance with the invention make possible a plurality of mutually independent functions. Additionally to the above-described stop function with the stop 7a, the stop device 6 is rapidly and readily manipulably adjustable between a use position and a non-use position. For this purpose, there is needed solely a manual rotation of the stop device 6 around the holding pin 16. By this means, the stop device 6 is not only prevented from functioning, but also the view of the treatment site is improved. By means of a pivoting to the one or the other side of the handpiece 1, the arrangement can be set selectively also as a left-handed or right-handed configuration.

The latching device V or plug-in/clamping frame ST makes it possible to equip the handpiece 1 readily manipulably and rapidly with the stop device 6, or to remove the stop device 6. Such a removal can also be considered to be an adjustment to the non-use position.

The configurations in accordance with the invention are very advantageously suitable for treatment sites in the restricted mouth region and in particular for tooth canal treatment with elongate tooth canal tools. They are suitable, however, inter alia also for such handpieces as are used in a medical or dental laboratory for the working of models or the like.

What is claimed is:

1. A handpiece for use with a penetration tool, conspiring:
    a connection device, arranged in a forward end region of the handpiece, adapted to connect to the penetration tool; and
    a settable stop device adapted to limit the penetration depth of the tool, the settable stop device including a guide and a stop part adjustable in the guide longitudinally of the penetration depth of the tool, wherein the stop part is formed of a hard elastically bendable material and sits in the guide bowed so far that its return bending force gives rise to a clamping force and is secured in a respective adjusted position by the clamping force;
    wherein the clamping force is elastic and is great enough that it secures the stop part against displacing forces effective in functional operation of the too but not great enough to prevent the stop part from being manually displaced.

2. The handpiece of claim 1, wherein the stop part is a pin-shaped component having a round cross-sectional form.

3. The handpiece of claim 1, wherein the guide includes a hollow tube having a forward limb extending substantially parallel to the penetration depth of the tool and a rearward limb extending in an angled or curved manner.

4. The handpiece of claim 1, wherein the stop part is adjustable transversely of the penetration depth of the tool and is secured in the respective adjusted position by a clamping part against an unintended displacement.

5. The handpiece of claim 4, wherein the clamping part is subject to an elastic clamping tension great enough that the clamping part is secured against displacing forces effective in functional operation of the tool but not great enough to prevent the stop part from being manually transversely adjustable.

6. A handpiece for use with a penetration tool, comprising:
    a connection device, arranged in a forward end region of the handpiece, adapted to connect to the penetration tool; and
    a stop device adapted to limit the penetration depth of the tool, the stop device including a stop part which is adjustable transversely of the penetration depth of the tool and is secured in a respective adjusted position against an unintended displacement by a clamping part;
    wherein the clamping part has an elastic clamping tension great enough that it secures the stop part against displacing forces effective in functional operation but not great enough to prevent the stop part from being manually adjustable and wherein the clamping part further comprises a C-shaped clasp arranged on a holding pin having a circular or cornered cross-sectional shape.

7. The handpiece of claim 6, wherein the stop part is rotatable about a middle axis of the tool.

8. The handpiece of claim 6, wherein the holding pin includes a coaxial sleeve shaped projection surrounding the tool or the connection device.

9. A handpiece for use with a penetration tool, comprising:
    a connection device, arranged in a forward end region of the handpiece, adapted to connect to the penetration tool; and
    a stop device adapted to limit to the penetration depth of the tool, the stop device including a stop part which is adjustable longitudinally and/or transversely of the penetration depth of the tool and is secured in a respective adjusted position by a clamping force, the stop device being connectable with, and releasable from, the handpiece by the use of a latching device;
    wherein the latching device is formed by a holding pin and a transversely or axially insertable clasp and wherein the holding pin is formed by a co-axial sleeve-shaped projection surrounding the tool or the connection device.

\* \* \* \* \*